United States Patent [19]

Karell

[11] Patent Number: 5,507,278
[45] Date of Patent: Apr. 16, 1996

[54] TONGUE-GUARD FOR INHALER

[76] Inventor: Manuel L. Karell, 3573-22 St., San Francisco, Calif. 94114

[21] Appl. No.: 342,214

[22] Filed: Nov. 18, 1994

[51] Int. Cl.⁶ .................................................. A61M 15/00
[52] U.S. Cl. ........................................ 128/200.23; 604/77
[58] Field of Search ...................... 128/200.14, 200.15, 128/200.18, 200.22, 200.23, 204.11, 203.23; 604/77, 201.26, 207.14, 207.15

[56] References Cited

U.S. PATENT DOCUMENTS

| | | | |
|---|---|---|---|
| 327,237 | 9/1885 | Clark | 128/200.15 |
| D. 348,928 | 7/1994 | Ashley | 128/200.14 |
| D. 349,572 | 8/1994 | Jagnandan | 128/200.23 |
| 3,854,478 | 12/1974 | Cunningham | 604/77 |
| 4,470,412 | 9/1984 | Nowacki | 128/200.18 |
| 4,738,662 | 4/1988 | Kalt et al. | 128/DIG. 26 |
| 5,181,505 | 1/1993 | Lew et al. | 128/200.26 |
| 5,195,513 | 3/1993 | Sinko et al. | 128/200.26 |
| 5,318,523 | 6/1994 | Lu | 604/77 |
| 5,331,953 | 7/1994 | Anderson | 128/200.14 |
| 5,341,801 | 8/1994 | Zenchner | 128/203.15 |

Primary Examiner—Edgar S. Burr
Assistant Examiner—William J. Deane, Jr.

[57] ABSTRACT

An inhaler for asthma and other medical conditions consists of a medicine canister (12), and a canister holder (10). Tongue Guard for Inhaler (20) is attached onto the canister holder, and assists user in placing inhaler into proper position. When the inhaler is activated, flow of medicine is diverted away from tongue, and settling of medicine on tongue is prevented. Tongue Guard for Inhaler prevents medicine from settling on tongue, thereby preventing bad taste and injury to tongue, such as atrophy. It can be used in conjunction with spacer devices or it can be built integrally within canister holder.

2 Claims, 3 Drawing Sheets

Front View

TONGUE-GUARD FOR INHALER

BACKGROUND—FIELD OF INVENTION

The present invention relates generally to medical devices, and specifically to be used in conjunction with a medicine dispenser of the inhaler type that is used for asthma and other medical conditions.

BACKGROUND— DESCRIPTION OF PRIOR ART

Many types of inhalers are currently in use for respiratory conditions such as asthma. Most utilize a medicine canister holder, such as the devices in U.S. Pat. No. 5,331,953 to Andersson, 1994, and U.S. Pat. No. Des. 349,572 to Jagnandan, 1994. Other devices fit onto the medicine canister holder, such as U.S. Pat. No. 4,470,412 to Nowacki, 1984, marketed as the AEROCHAMBER.

SUMMARY OF THE INVENTION

Medicines dispensed via inhalers can settle on the tongue causing bad taste, and injury to the tongue such as atrophy. Also, the inhaler needs to be positioned correctly for best results. Tongue Guard for Inhaler fits around the mouth piece of the canister holder. Tongue Guard for Inhaler diverts medicine flow away from tongue, and prevents the medicine from settling on the tongue surface. Tongue Guard for Inhaler assists placement of inhaler for proper functioning, and can be used on spacers such as AEROCHAMBER.

DETAILED DESCRIPTION OF THE PREFERRED EMBODIMENT

Figure 1:
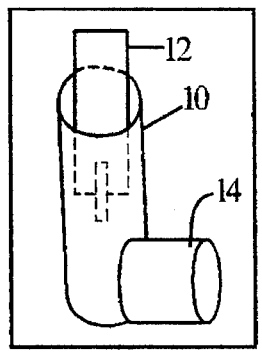
FIG. 1 is a plano-perspective drawing of a medicine canister holder.
Figure 2:
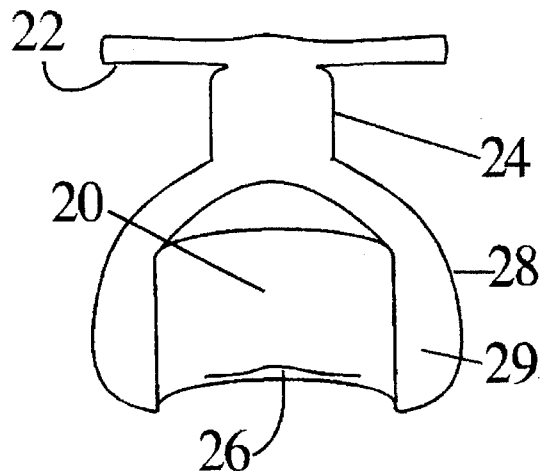
FIG. 2 is a top down drawing of Tongue Guard for Inhaler.
Figure 2A:
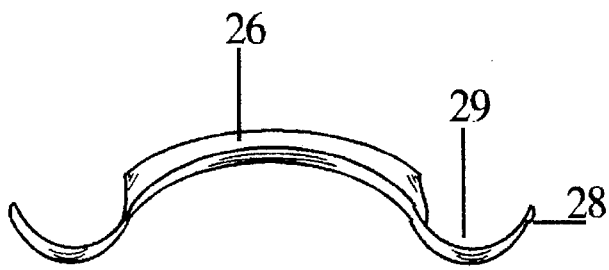
FIG. 2A is a front view of the Tongue Guard Inhaler.
Figure 3:
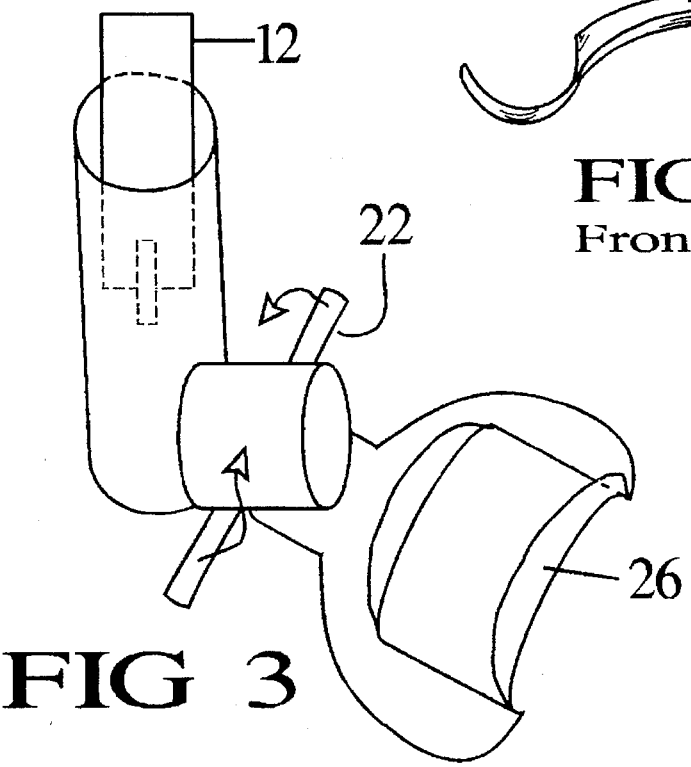
FIG. 3 is a plano-perspective drawing of Tongue Guard for Inhaler placed into position onto the mouth piece of a canister holder.
Figure 4:
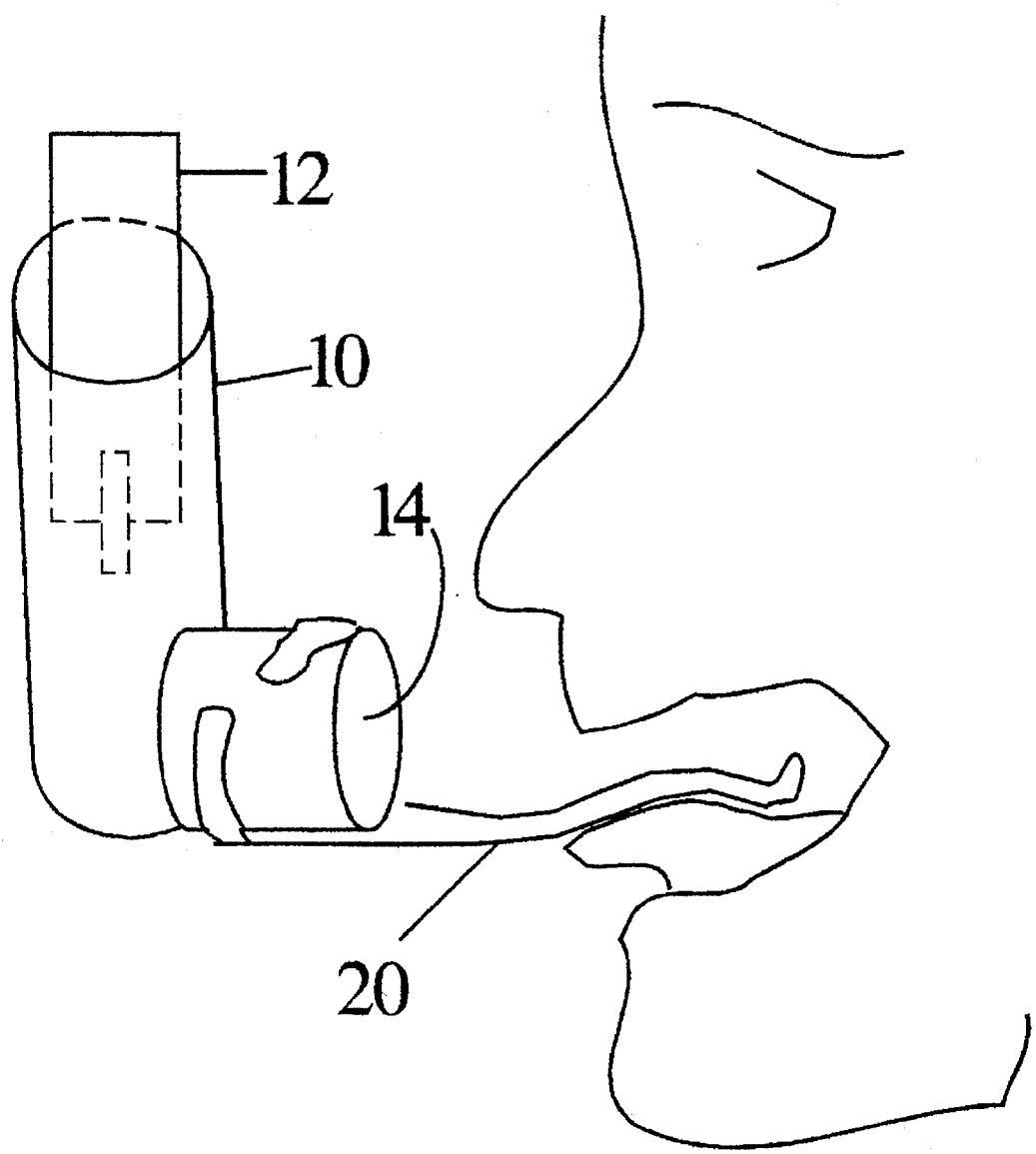
FIG. 4 is a schematic of use of Tongue Guard for Inhaler.
Figure 5:
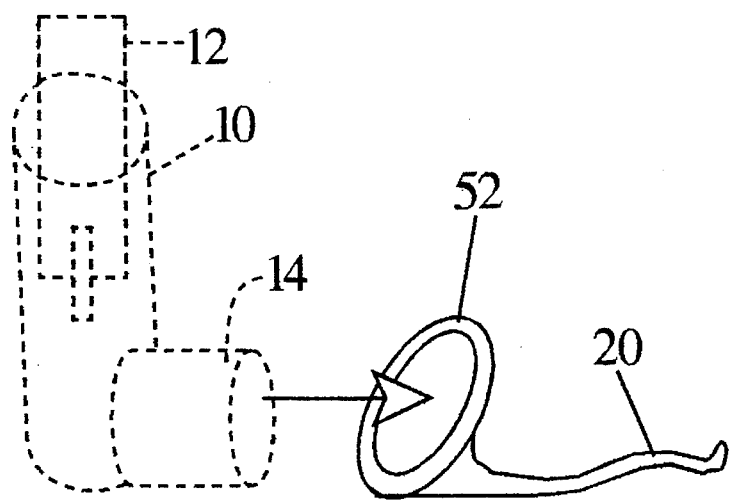
FIG. 5 shows details of alternate attaching means.
Figure 6:
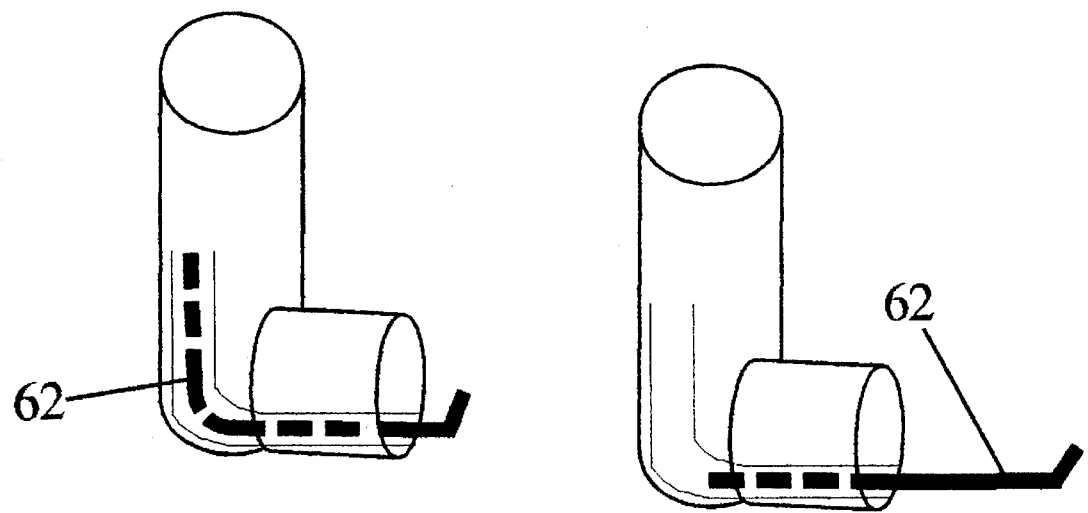
FIG. 6 shows details of Tongue Guard for Inhaler integrally built within canister holder.

FIG. 1 shows an inhaler for asthma and other medical conditions which consists of a medicine canister (12), and a canister holder (10). Tongue Guard for Inhaler is attached onto (FIG. 3) said canister holder (10) by attaching means, such as neck tabs (22) of FIG. 2, such that, the neck (24) of tongue guard (20) rests below opening of mouthpiece (14) of canister holder (10). When the inhaler is activated, flow of medicine is diverted away by protruding lip (26) and side channels (29), settling of medicine on tongue is prevented by body (28) of tongue guard (20) resting over tongue. Tongue Guard for Inhaler assists proper inhaler placement by having a certain measured length derived by the combined lengths of body (28) and neck (24). Another attaching means (FIG. 5) is shown by having an elastomeric nature of attaching means (52). An additonal alternative is to have tongue guard (62) integrally built within (FIG. 6) canister holder.

While the above description contains many specificities, these should not be construed as limitations on the scope of the invention but as merely providing illustrations of some of the presently preferred embodiments of this invention. For example, the means to attach can be accomplished with VELCRO, or can be attached to body instead of mouthpiece; and the means to divert may be other than a protruding lip. Thus the scope of the invention should be determined by the appended claims and their legal equivalents, rather than by the examples above.

I claim:

1. A guard for use with an inhaler comprising: a body having a first end anatomically shaped to fit within a mouth and over a tongue of a user, said body having a second end including means for attachment to an inhaler, a protruding lip located on the first end of said body and extending substantially perpendicular to the flow from an inhaler, said body including side channels, which in combination with said lip divert medicament away from a user's tongue, a neck located on the second end of said body, said neck supporting said means for attachment to an inhaler, whereby a combination of lengths of said body and said neck assist in proper placement of an inhaler from a mouth of a user.

2. An apparatus of claim 1 in which said guard is unitary with an inhaler.

* * * * *